United States Patent
Benner (10) Patent No.: US 10,106,837 B1
(45) Date of Patent: Oct. 23, 2018

(54) PROCESSES FOR POINT OF CARE DETECTION OF DNA AND RNA

(71) Applicant: Steven A Benner, Gainesville, FL (US)

(72) Inventor: Steven A Benner, Gainesville, FL (US)

(*) Notice: Subject to any disclaimer, the term of this patent is extended or adjusted under 35 U.S.C. 154(b) by 0 days.

(21) Appl. No.: 14/613,960

(22) Filed: Feb. 4, 2015

Related U.S. Application Data (60) Provisional application No. 61/935,921, filed on Feb. 5, 2014.

(51) Int. Cl.
*C12Q 1/68* (2018.01)
*C12Q 1/6806* (2018.01)
*C12N 15/10* (2006.01)
*C12Q 1/6844* (2018.01)

(52) U.S. Cl.
CPC ......... *C12Q 1/6806* (2013.01); *C12N 15/101* (2013.01); *C12Q 1/6844* (2013.01)

(58) Field of Classification Search
None
See application file for complete search history.

(56) References Cited

U.S. PATENT DOCUMENTS

| | | | | |
|---|---|---|---|---|
| 3,301,767 | A * | 1/1967 | Laufer | C07H 1/00 424/94.61 |
| 6,245,238 | B1 * | 6/2001 | Agner | B01D 15/08 210/198.2 |
| 7,026,468 | B2 * | 4/2006 | Nochumson | B01D 15/327 536/23.1 |
| 9,057,673 | B2 * | 6/2015 | Rogacs | G01N 1/34 |
| 2006/0024712 | A1 * | 2/2006 | Baker | C12N 1/06 435/6.16 |
| 2011/0124053 | A1 * | 5/2011 | Benner | C12Q 1/686 435/91.2 |

FOREIGN PATENT DOCUMENTS

WO   WO2012009627 A  *  1/2012

OTHER PUBLICATIONS

Pecson et al. A real-time PCR method for quantifying vaible Ascaris eggs using first internally transcribed spacer region of ribosomal RNA. Applied and Environmental Microbiology, vol. 72 (12), p. 7864-7872, 2006.*

* cited by examiner

*Primary Examiner* — Suryaprabha Chunduru (57) ABSTRACT

This invention provides a single process that collects any and all target nucleic acids from a sample that can contain any of a number of biological species, including bacteria, viruses, or fungi, where the first step renders the sample nonhazardous and releases nucleic acids from cell structures, compartments, and molecular complexes that may hold them, the second step concentrates the target nucleic acids from even very highly dilute states, in the third step releases these in a form that, following dilution, makes them compatible with processes that amplify nucleic acids, both standard PCR as well as isothermal amplification protocols. The pre-amplification process involves ammonia solutions no more toxic than those found in the commercial product Windex, requires no electrical power, requires materials no more complex than water desalinization resin and salt, and can be used by inexperienced individuals.

11 Claims, 6 Drawing Sheets
Specification includes a Sequence Listing.

SEQUENCE LISTING

```
<160> NUMBER OF SEQ ID NOS: 4

<210> SEQ ID NO 1
<211> LENGTH: 84
<212> TYPE: DNA
<213> ORGANISM: Artificial Sequence
<220> FEATURE:
<223> OTHER INFORMATION: Synthetic

<400> SEQUENCE: 1
accatgctaa acacagtggg gggacatcaa gcagccatgc aaatgttaaa agagaccatc    60
aatgaggaag ctgcagaatg ggat                                          84

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
accatgctaa acacagtggg gggaca                                        26

<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
atcccattct gcagcttcct cattgat                                       27
```

```
<210> SEQ ID NO 4
<211> LENGTH: 27
<212> TYPE: DNA
<213> ORGANISM: Artificial Sequence
<220> FEATURE:
<223> OTHER INFORMATION: Synthetic

<400> SEQUENCE: 4
atcccattct gcagcttcct cattgat                                          27
```

PROCESSES FOR POINT OF CARE DETECTION OF DNA AND RNA

CROSS REFERENCE TO RELATED APPLICATIONS

This application claims the priority of Benner, S. A. (2014) Processes for Point of Care Detection of DNA and RNA. Provisional U.S. Patent Application 61/935,921 (Filed Feb. 5, 2014)

STATEMENT REGARDING FEDERALLY SPONSORED RESEARCH OF DEVELOPMENT

This invention was made with government support under HDTRA1-13-1-0004 awarded by the Defense Threat Reduction Agency. The government may have certain rights in the invention.

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

For many practical applications, it is desirable to detect small numbers of DNA or RNA molecules (collectively xNA) that have a pre-selected sequence from substantial volumes of liquid. For example, xNA molecules from bacteria present in urine can indicate a urinary tract infection. xNA molecules from norovirus from washings from a cruise ship cabin can indicate that decontamination has been incomplete. This requires a step in a workflow process that disrupts cellular and supramolecular structures that may hold the xNA. It also requires a concentration step so as to allow xNA molecules that may be dispersed throughout the substantial volume to be concentrated into a smaller volume. Then, it requires an amplification principle that will create a detectable signal from the very few xNA molecules that might be present in the sample.

At present, procedures to do so involve expensive capture supports, such as those sold by Qiagen, which can cost dollars per sample. Nearly all the workflows associated with these processes include instruments such as centrifuges. Further, since the sample contains (or might contain) a biohazardous microorganism, virus, or other pathogen, it must be run by highly trained personnel.

The realities of modern infectious disease require inventions to do similar things but in low resource environments, at points of sampling, with substantially untrained personnel, and at very low cost. For example, during the Ebola panic, any vomit in airports was potentially a biohazardous substance capable of transferring the disease to maintenance staff and cleanup individuals. Similarly, in high school or college infirmaries, immediate decisions must be made with respect to exotic respiratory viruses, where neither the cost of a Qiagen kit nor the technical expertise needed to handle it are available. Similarly, first responders (such as ambulance personnel) need to be able to evaluate the potential hazards of the pathogen on-site, where the nucleic acid sequence is the defining feature of the pathogen.

BRIEF SUMMARY OF THE INVENTION

This invention allows the collection of nucleic acids from a sample in a process where the first step renders the sample nonhazardous, making it suitable for use by inexperienced individuals. This is done by treating the sample with ammonia and (in some embodiments) detergent. Further, the alkalinity of an ammonia sample (and, optionally, detergent) disrupts cell structures to release the nucleic acids from compartments that may hold them. Further, the alkalinity disrupts folder structure and duplex structures of DNA and RNA. The result is a sample that no longer is infectious for a wide range of potential pathogens.

The invention necessarily couples this sample preparation step to a step whereby the disrupted sample is passed through a poly-cationic solid support. While not wishing to be bound by theory, it is speculated that coulombic interactions between the poly-cationic support and the poly-anionic xNA molecules captures the poly-anionic xNA molecules on the support. Further, the poly-cationic support is itself self-sterilizing with respect to many bacteria.

This capture step is necessarily coupled to a third step, in which the captured xNA is released from the support bypassing for the support a solution of salt. This delivers the xNA into a capture volume that is available for downstream xNA detection. In some samples, the xNA is sufficiently abundant to allow its detection directly. Preferable approaches include hybridization in capture, including in branched nucleic acid assays, especially those that incorporate components of an artificially expanded genetic information systems (AEGIS).

Alternative approaches must be applied if the concentration of xNA is too low to allow direct detection. These include amplification steps, such as the polymerization chain reaction (PCR) or and isothermal amplification method such as the helicase-dependent amplification (HDA) or the recombinase-polymerase amplification (RPA) process. Here, the high concentrations of salt needed to elute the xNA are generally incompatible with the enzymes used in these amplification processes. In this case, a necessary part of the process involves mixing the eluate with a volume of amplification "master mix" that dilutes the total concentration of salt to a concentration is acceptable to those enzymes, typically between 100 and 150 mM.

Last, when isothermal amplification is the option chosen, then a new form of nucleic acids known as self-avoiding molecular recognition systems are preferably used to ensure that the amplification is successful.

DETAILED DESCRIPTION OF THE INVENTION

A process that recovers scarce nucleic acid molecules in unknown compartments from dilute solution to prepare them for amplification must incorporate the following components:

(a) A disruption principle. In that sample, xNA molecules cannot be assumed to be in a position able to do hybridization. Indeed, the xNA species of interest are nearly always tied up in complexes that prevent their doing so to externally added primers and probes. Therefore, for any assay to work, especially one in low resource environments (LREs), the xNA complexes must be disrupted to make xNA accessible to Watson-Crickery. Heat is a common way to disrupt xNA complexes. However, heat is not preferred in LREs, as it requires power and experience, generally generates precipitates that are challenging to handle for a non-trained individual common especially one who does not have access to a centrifuge, and requires expertise to know how long to heat to render a sample sterile.

(b) A sampling principle. In reality, especially in low resource environments, sample is not a blood sample that is deliberately drawn by an expert professional. Rather, the most common fluids are those that are naturally expelled (such as urine, feces, vomitus, and sputum). Another common environment is one where target xNA is concentrated naturally (such as mosquitoes). Still other common environments might be soil samples or surface swabs. The art contains very few processes that address these, and none that address them all. On the contrary, most arts associate with nucleic acid targeted surveillance and diagnostics begins with the assumption of a sample of blood will be drawn in a doctor's office.

(c) A concentration principle. Outside of the doctor's office, is impossible to know the efficacy of a sampling procedure. A large volume of fluid, for example used to wash out a ship state room, or a public toilet, can contain very few of the nucleic acid molecules that indicate the presence of an infectious disease. Even so, these fluids can be biohazardous and, for both public health and individual diagnostics, provide extremely important information about the presence or absence of an infectious disease. Large sample volumes with few target molecules require concentration to support the needs of public health or personal diagnostics. Here again, the art has gone in the entirely opposite direction. For example, the nanotechnology community has advanced nano-instrumentation that seeks to detect the nucleic acids of infectious diseases from the volumes arising from, for example, a pin prick of blood. With such volumes being on the order of 50 µL or less, in with even for blood an interesting concentration of target nucleic acids being 10 per milliliter (this is, for example, the amount of HIV viral particles in a patient escaping remission) the statistical odds of finding even one target in the sample volume are low.

(d) An amplification principle. It is conceivable that concentration of xNA from a large volume into a small volume will lead to a concentration of molecules that can be directly detected. For example, the branched DNA diagnostics application, specifications of which are incorporated herein by reference, does so using DNA dendrimers without amplifying the target nucleic acid sequence at all. This instant invention does not exclude direct detection of this nature. More commonly, however, DNA amplification is necessary. The art contains many approaches to do so, including the polymerase chain reaction (PCR), and various isothermal amplification methods. Specifications for all these are incorporated herein by reference. Unfortunately, chemical methods that are used to sterilize biological samples can easily be incompatible with these amplification enzymes, unless the chemicals are removed. Further, in complex biological mixtures containing many xNA species, special efforts must be taken to insure that background signals to not create false positives. To this end, artificially expanded genetic information systems and self avoiding molecular recognition systems can be used to obtain highly clean amplifications. The following patent applications that cover these in these applications are incorporated herein in their entirety by reference:

Benner, S. A. (2013) Amplification of oligonucleotides containing non-standard nucleobases. Ser. No. 13/740, 642 (Filed Jan. 14, 2013)

Benner, S. A., Sharma, N. (2013) Recombinase-based Amplification With Substitute Nucleotides. U.S. patent application Ser. No. 13/789,022 (Filed Mar. 7, 2013)

Benner, S. A., Yang, Z. (2013) Helicase Dependent Amplification of DNA Molecules Using Nucleotide Analogs. Application Ser. No. 13970111 (Filed Aug. 19, 2013)

Benner, S. A., Yang, Z. (2013) Polymerase Incorporation of Non-standard Nucleotides. U.S. Pat. No. 8,614,072 (Dec. 24, 2013) U.S. patent application Ser. No. 12/999,138 (Filed Dec. 15, 2010)

Benner, S. A., Sismour, A. M. (2013) Amplification of oligonucleotides containing non-standard nucleobases. U.S. Pat. No. 8,354,225 (Jan. 15, 2013) U.S. patent application Ser. No. 11/371,497 (Filed Mar. 3, 2006)

Benner, S. A., Hoshika, S., Chen, F. (2008) Self-Avoiding molecular recognition systems in DNA priming. U.S. patent application Ser. No. 12/229,159 (Filed Aug. 20, 2008)

The instant invention comprises these steps

1. Mixed a sample with a solution of ammonia (most preferred as 100 mM, or a concentration between 50 and 250 mM). If the sample is a liquid, the presently preferred amount of ammonia solution is equal to the volume of the sample. If the sample is a solid, then the sample is suspended in the ammonia solution directly. The presently preferred volume of the sample is approximately one milliliter. Detergent (preferably a non-ionic detergent at 0.1%) may also be present optionally.

2. While not wishing to be bound by theory, the ammonia does four things:

2.1 The ammonia sterilizes the sample, rendering it no longer a biohazard by disrupting any pathogens that the sample contains. In principle, these samples can be handled by inexperienced personnel, and can be shipped without hazard.

2.2 The ammonia releases all nucleic acids (including DNA and RNA, collectively called "xNA") from whatever compartment that holds them (such as cell, nucleus, ribosome, and chromosome), making substantially all xNA molecules available for capture.

2.3 The ammonia unfolds RNA and separates complementary strands of DNA into single strands, by deprotonating the thymine and guanine nucleobases, disrupting their ability to hydrogen bond to their complements adenine and cytosine, respectively.

2.4 The ammonia lightly fragments RNA molecules, allowing them to move more freely through sample preparation steps while preventing refolding to a structure that can no longer be invaded by primers and probes.

3. The mixture is then passed through a short cartridge (presently preferred to be approximately 1 cm long and 0.5 cm in diameter) containing a capture support that has cationic species immobilized to it. The presently preferred cationic species are quaternary ammonium ions, including trimethylammonium ions where the fourth bond to the ammonium nitrogen is a linker attaching the ammonium species to the support. These can be obtained by commercial suppliers as, for example, Q-Sepharose, Dowex 1, or other commercially available "strongly basic" anion exchange columns. The essential feature of quaternary ammonium ions is that they retain their positive charges even at the high pH of an ammonia solution. The support captures recovers >99% of the xNA in the sample.

4. The support is then washed with water (presently preferred between 2 and 5 mL) by passing water through the cartridge to render the sample essentially pH neutral.

The sample is now not biohazardous. It may now be shipped, if desired, as a nonhazardous package. It may be used by a nonmedical professional. The process continues as follows:

5. The captured xNA is eluted from the support by passing a solution of salt (presently preferred as sodium chloride, although other salts are equally effective, the presently preferred volume is 1 mL, the presently preferred concentration is 1 M, although a range of 0.8-2 M is also effective) through the cartridge. This elutes the xNA from the support, where the DNA is collected.

6. The collected eluate is then diluted with a master mix that contains the requisite materials needed to amplify nucleic acids, either in a PCR process or an isothermal amplification process. The dilution diminishes the concentration of salt to a level that is compatible with the amplification process, including the enzymes that will be use in that process.

7. PCR or an alternative isothermal procedure is applied to the diluted mixture, allowing identification of the presence of target xNA. The presently preferred application processes are PCR, helicase dependent amplification, and recombinase-polymerase amplification. If the xNA species to be detected is RNA, and the amplification process includes a reverse transcriptase, as is well known in the art.

8. Optionally, the amplification process can incorporate one of two nucleic acid innovations, or both together. These are "artificially expanded genetic information systems" (AEGIS) and self-avoiding molecular recognition systems (SAMRS). AEGIS and SAMRS are covered by their own patent applications, as cited above. Further, in the presently preferred embodiment of the instant invention, they are used in a nested PCR format, where SAMRS components are placed at sites at or near the 3'-end of primers (most preferably, four SAMRS components are placed in four sites at the very end of the primer, excluding the 3'-site) that are either used as such, or that also carry a 5'-tag containing AEGIS components. In the second case, the presently preferred embodiment is a nested PCR architecture, where initially generates an amplicon that carries 5'-AEGIS tags, with the PCR later being carried by external primers that comprise only the AEGIS tag.

Steps one through six are themselves considered to be inventive, as a nonobvious combination of both known and novel processes. Further, as outlined in the examples, they lead to surprising results, since they allowed detection of HIV RNA from virus particles, ribosomal RNA from whole fungal cells, and genomic DNA from whole fungal cells, without requiring centrifugation or other technical equipment or expertise. This shows the same denaturation procedure not only releases nucleic acids from virus particles, it also releases nucleic acids from tightly and compactly bound ribosomes, which normally do not offer their nucleic acids to primers for binding, and also releases nucleic acids from the nucleus of normally robust fungus cells. Indeed, Example 4 shows that bacterial genomic DNA can also be recovered and amplified using the single process. It is surprising that this single process, involving no instrumentation, no technical skill, and no electrical power can recover nucleic acids in detectable form from the fungal nucleus, the fungal ribosome, retrovirus particles, and bacterial cells.

Further, as shown in the examples, it was surprising to see that the material recovered from the poly-cation support could be using both isothermal amplification processes, as well as in standard PCR. Isothermal amplification processes are especially well suited for low resource environments.

EXAMPLES

Example 1: Detection of HIV RNA that is Sterilized, Concentrated, Recovered, and Amplified by the Isothermal Helicase-Dependent Amplification (HDA) Process Experimental Design:

The sample here was HIV-1 RNA Quant, Human Immunodeficiency Virus (Subtype B, Catalog #: 42103)(500 copies/µL) mixed with synthetic urine (50 mL of $H_2O$, 0.47 g urea, 0.15 g NaCl, 34 mg creatinine, 0.05 g $KH_2PO_4$, and 0.025 g ammonium bicarbonate, pH=7). Following sterilization by mixing with a 1 mL sample with an equal volume of 100 mM ammonia, the mixture was passed through a poly-cationic (quaternary ammonium salt) Q-Sepharose column where the xNAs were captured by the positive charged support. The support was washed with water. Then, the captured xNA molecules were eluted with 50 µL of 1 M NaCl solution.

REFERENCE

David F. Putnam, composition and concentrative properties of human urine. NASA contractor report. 1802, July 1971.

The target was the following Sequence from the gag region:

```
                                        SEQ ID NO 1
ACCA TGCTAAACAC AGTGGGGGGA CATCAAGCAG CCATGCAAAT

GTTAAAAGAG ACCATCAATG AGGAAGCTGC AGAATGGGAT
```

The underlined sequences are primers and probe binding sequences.

The primers for asymmetric HDA were:

```
                                        SEQ ID NO 2
GagF_Std_26mer:
5'-ACCATGCTAAACACAGTGGGGGGACA-3' (final 50 nM)

SEQ ID NO 3
GagR_Std_27mer:
5'-ATCCCATTCTGCAGCTTCCTCATTGAT-3' (final 150 nM)

SEQ ID NO 4
GagR_Std_27mer:
3'-TAG TTA CTC CTT CGA CGT CTT ACC CTA-5' (final 50 nM)
```

Components of self-avoiding molecular recognition systems (SAMRS) are incorporated at four position at the 3'-end, excluding the very 3'-terminal nucleotide. That is, in Sequence Identification numbers 2, 3, and 4, the SAMRS nucleotides were respectively GGAC, TTGA, and CCCT. The experimental asymmetric HDA assays included controls as well, as in the following table.

| Components | HIV-1 RNA 1000 copies | HIV-1 RNA 100 copies | HIV-1 RNA eluted from column | Negative Control | Final Conc. |
|---|---|---|---|---|---|
| $dH_2O$ in primer mix | 2 μL | 2 μL | 2 μL | 2 μL | 25 μL |
| 1'. GagF-Std-26 mer (10 μM) | 0.125 μL | 0.125 μL | 0.125 μL | 0.125 μL | 50 nM |
| 2'. GagR-Std-27 mer (10 μM) | 0.375 μL | 0.375 μL | 0.375 μL | 0.375 μL | 150 nM |
| HIV-1 RNA (500 copies/μL, asuragen) | 2 μL | | | | 1000 copies/25 μL |
| HIV-1 RNA (50 copies/μL, asuragen) | | 2 μL | | | 100 copies/25 μL |
| HIV-1 RNA (~80 copies/μL, in 1M NaCl from Kristen received on Sep. 11, 2014) | | | 1 μL | | ~80 copies/25 μL |
| $H_2O$ in target RNA or in negative control | 9.5 μL | 9.5 μL | 10.5 μL | 11.5 μL | |
| NaCl (500 mM) | 2 μL | 2 μL | 40 mM (from elution buffer 1M NaCl) add 2 μL of H2O | 2 μL | 40 mM |
| $MgSO_4$ (100 mM) | 1.25 μL | 1.25 μL | 1.25 μL | 1.25 μL | 5 mM or 4 mM |
| IsoAmp dNTP Solution | 2 μL | 2 μL | 2 μL | 2 μL | 1.14× |
| 10× Annealing Buffer II | 2.5 μL | 2.5 μL | 2.5 μL | 2.5 μL | 1× |
| IsoAmp Enzyme Mix III (BioHelix) | 2 μL | 2 μL | 2 μL | 2 μL | 2× |
| Rnase Out | 1 μL | 1 μL | 1 μL | 1 μL | 2× |
| Enhanced Avian RT (Sigma, 20 U/μL) | 0.2 μL | 0.2 μL | 0.2 μL | 0.2 μL | 0.64 U/μL |

Note:
NaCl (2 μL, 500 mM) were added to HIV-1 RNA controls and negative controls. However, NaCl (2 μL, 500 mM) were not added to samples eluted off column, because the elution buffer has 1M of NaCl. Lowering this concentration is the goal of the dilution. All assays were run at 65° C., for 120 min and were performed as triplicates.

Figure 1:
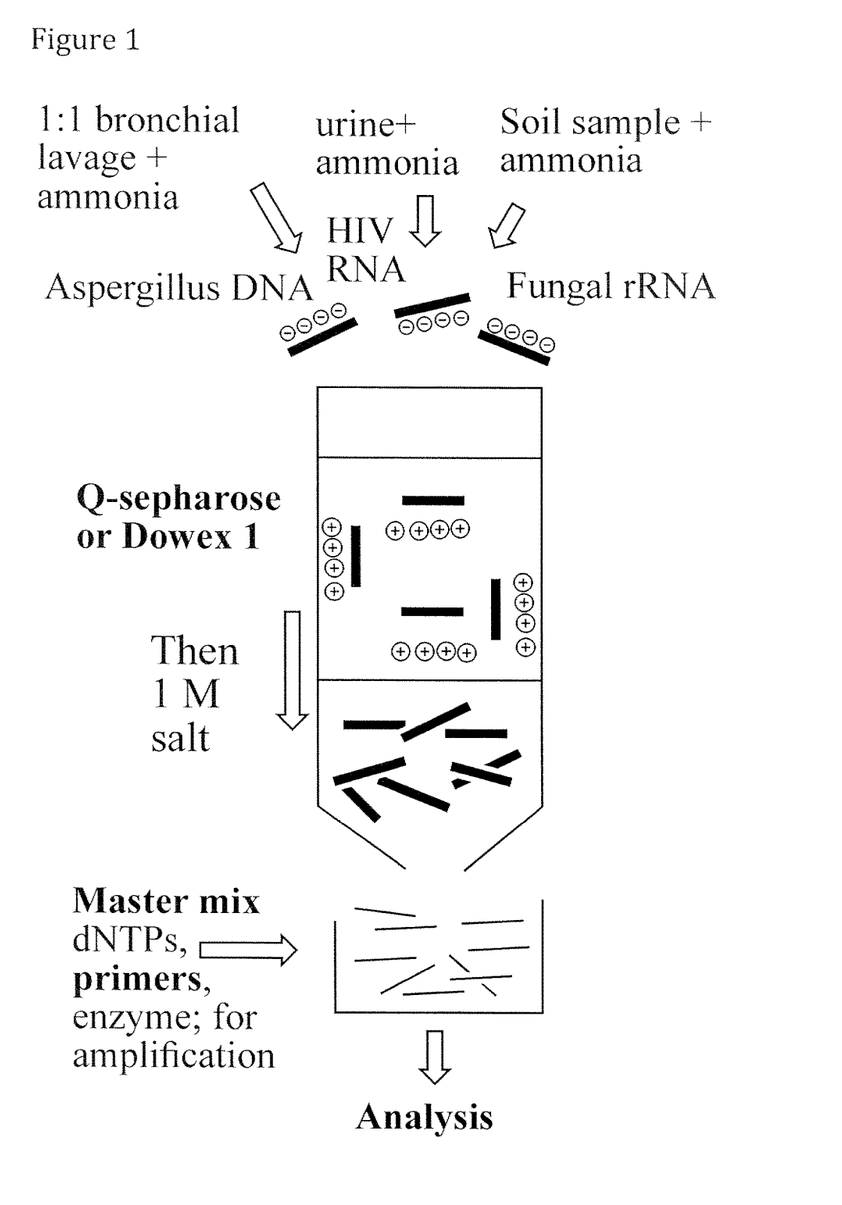
FIG. 1. A schematic view of the process of the claimed invention
Figure 2:
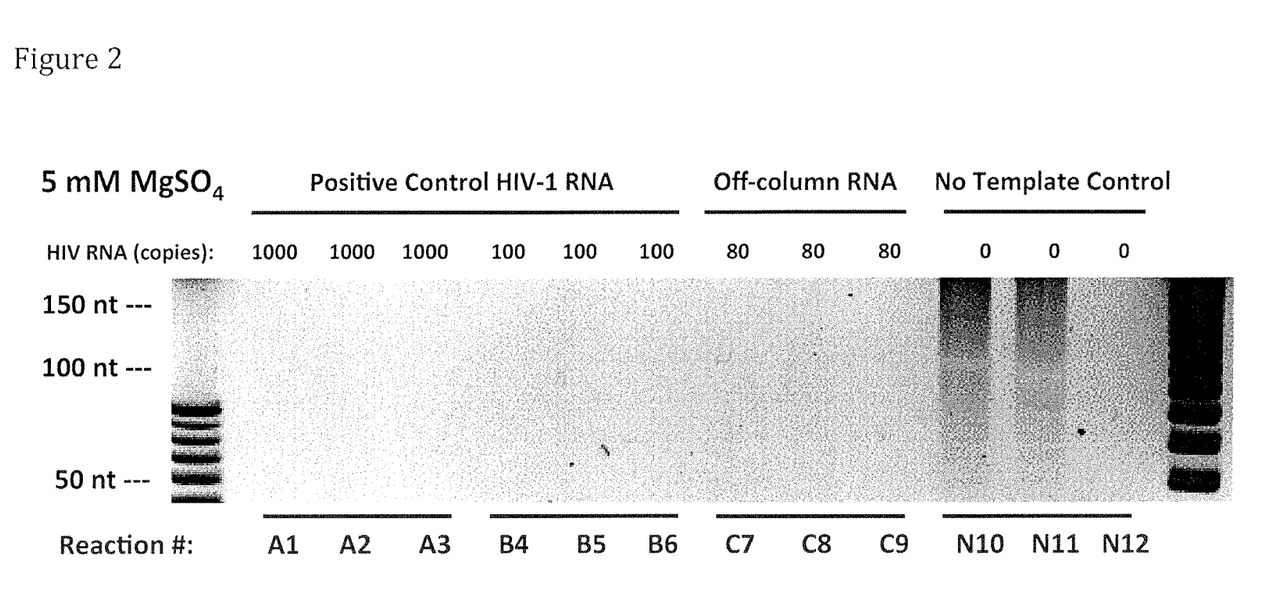
FIG. 2. A gel showing helicase-dependent amplification (HDA, in its reverse transcriptase mode) of RNA from HIV captured from dilute ammonia solution without detergent by the process of the instant invention. The products are resolved on 3% agarose, then showed the surprising result of quite efficient signal detection equal to or better than results obtained by direct analysis.

Results:

These results demonstrated that 1000, 100, and ~80 copies of HIV-1 RNA eluted from Q-Sepharose column with 1 M of NaCl can be isothermally amplified by asymmetric HDA (asHDA) using 50 nM of forward primer and 150 nM of reverse primer. The asymmetric HDA products were resolved on 3% agarose gel (FIG. 2). The key surprising result is in the "oft column RNA" lanes labeled C7, C8, and C9.

Example 2: Detection of Chromosomal DNA from Fungus RNA that is Sterilized, Concentrated, Recovered, and Amplified by PCR AEGIS-SAMRS primers were synthesized that target the chitin synthase gene (isoform 2) from multiple fungi, including *Coccidioides posadasii* and *Coccidioides immitis* (tested as a single pathogen due to their evolutionary closeness), *Paracoccidioides brasiliensis, Ajellomyces capsulatus*, and *Ajellomyces dermatitidis, Aspergillus terreus*, and *Botryotinia fuckeliana.*

These were set up to do a nested PCR architecture. All of the primers therefore had a common 5' common sequence containing nucleotides from an artificially expanded genetic information system (AEGIS) and, at their 3'-ends, nucleotides from a self avoiding molecular recognition system (SAMRS). AEGIS assists in "ultraclean" low noise amplification; SAMRS assists in obtaining problem-free multiplexing.

The sample was in dilute form in a simulant for a biological fluid. This was mixed with ammonia as in the claimed procedure, captured on Q-Sepharose, eluted with a 1 M sodium chloride solution, diluted into a master mix suitable for PCR but absent the salt so that the dilution volume lowered the concentration of salt to a level compatible with the enzymes in the PCR. 30 cycles of PCR were then performed.

Figure 3:
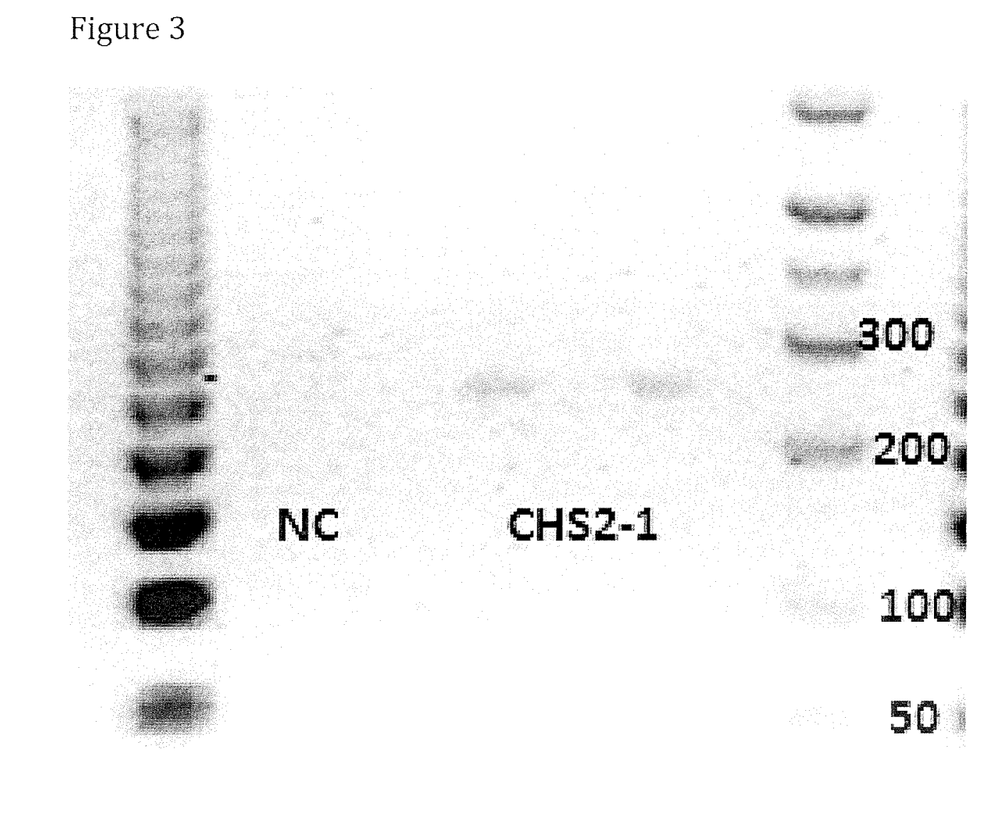
FIG. 3. A gel showing PCR amplification of DNA HIV captured from dilute ammonia solution without detergent by the process of the instant invention where the ammonia was applied to *Aspergillus* cells. Here, the PCR primers were targeted at a chitin synthase gene (isoform 2), and again show surprisingly effective detection of that gene sequence, and therefore the *Aspergillus* cells from a dilute solution by the process of the instant invention. *Aspergillus* causes a common fungal malady known is aspergillosis, FIG. 4. A gel showing the detection by reverse transcriptase PCR of ribosomal RNA from *Aspergillus* cells, where those cells were again disrupted and their content xNA recovered, concentrated, and released by the process of the instant invention. Here, the result is especially surprising since ribosomal RNA is expected to be folded, and therefore resist invasion by primers, and invasion is necessary for PCR amplification.

The results are shown in the gel in FIG. 3. The lane labeled NC indicates a control with no template. The outside lanes are markers with the indicated nucleotide lengths. The lanes labeled CHS2-1 show the amplicons arising from the CHS2 genes, obtained at two different concentrations of magnesium.

Figure 4:
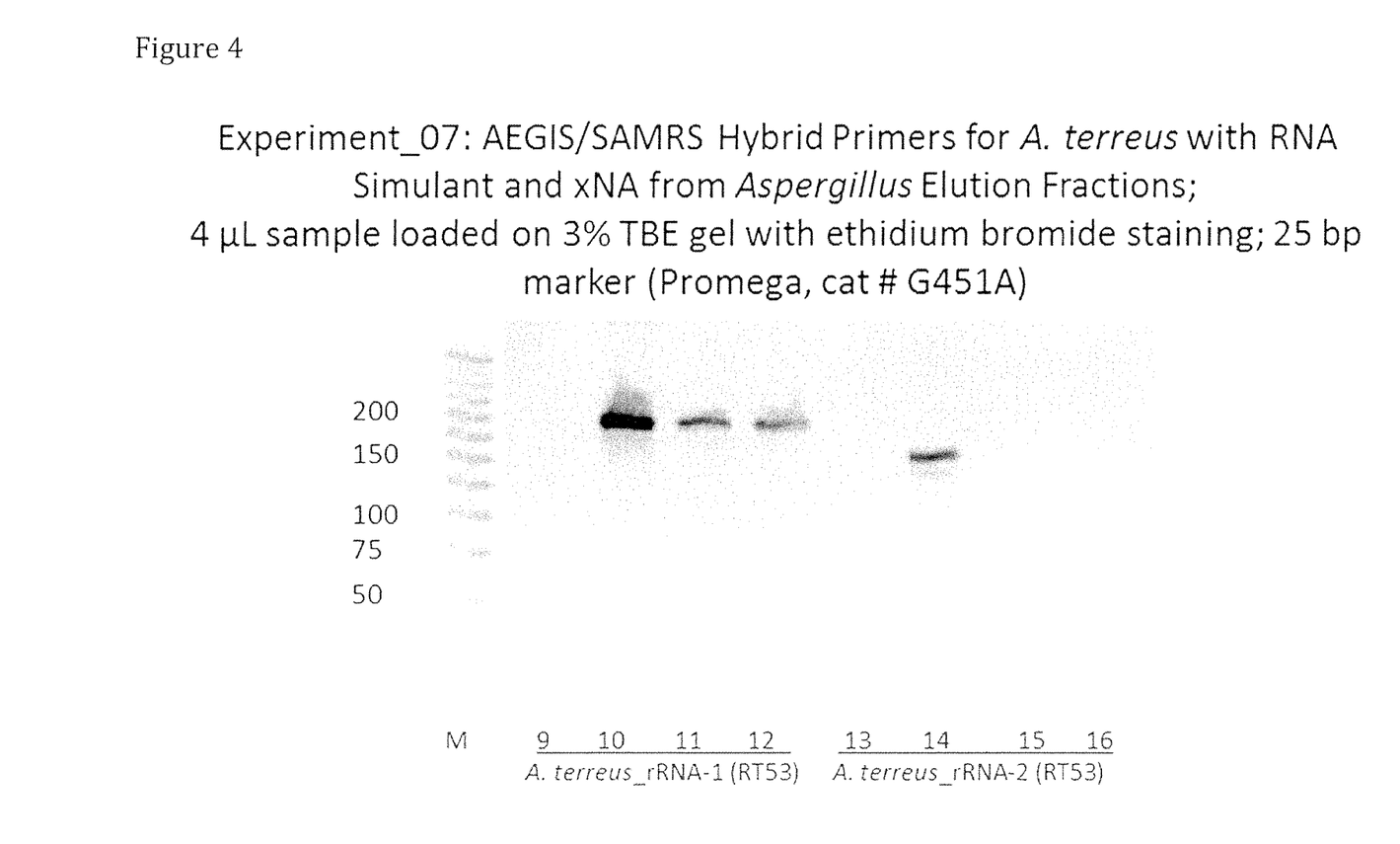
Figure 5:
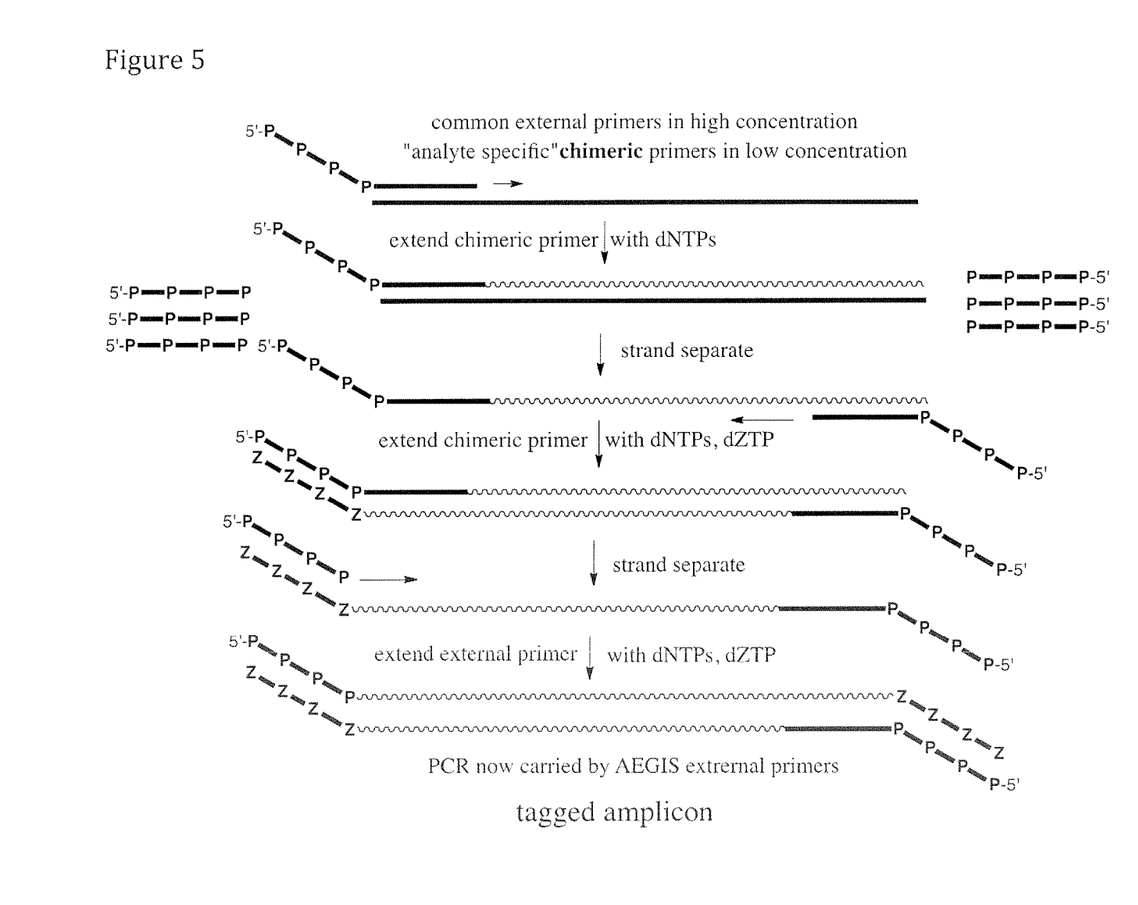
FIG. 5. A schematic showing a nested PCR architecture, where approximately four SAMRS components are placed at or near the 3'-end of the primers that are substantially complementary to the target xNA molecule to be amplified, with the primers carry a 5'-tag that contains one or more AEGIS components, here P, which is 2-amino-8-(1'-β-D-2'-deoxyribofuranosyl)-imidazo[1,2-a]-1,3,5-triazin-4(8H)-one).

Example 3. Proof that the Sample Preparation Procedure Followed by Cationic Capture Makes Ribosomal RNA Also a Suitable Target The sample was *Aspergillus* cells dispersed in a simulant for a biological fluid. They were mixed with 100 mM ammonia without detergent. The mixture was then passed through a Q-Sepharose column to capture total xNA. The captured xNA was then eluted with 1 M NaCl solution. Fractions (E1 through E9) were collected. Separate and combined fractions were then subjected to reverse transcriptase PCR. The results are shown in FIG. 4, with the lanes labeled as follows:

M=Marker

Lane 9: Primers only; this serves as a negative control

Lane 10: The first set of primers targeting the ribosomal RNA, plus rRNA simulant, which is a fragment of the ribosomal RNA that cannot fold as a complete ribosome. This serves as a positive control.

Lane 11: PCR using rRNA-1 primers, to which has been added material recovered from Q-Sepharose after sample preparation process of the instant invention. The bands show successful amplification of the rRNA molecules sample fraction E2

Lane 12: PCR using rRNA-1 primers, to which has been added material recovered from Q-Sepharose after sample preparation process of the instant invention. The bands show successful amplification of the rRNA molecules sample where all the collected fractions were combined.

Lane 13: Primers only; this serves as a negative control

Lane 14: The second set of primers targeting the ribosomal RNA, plus rRNA simulant Example 4

Figure 6:
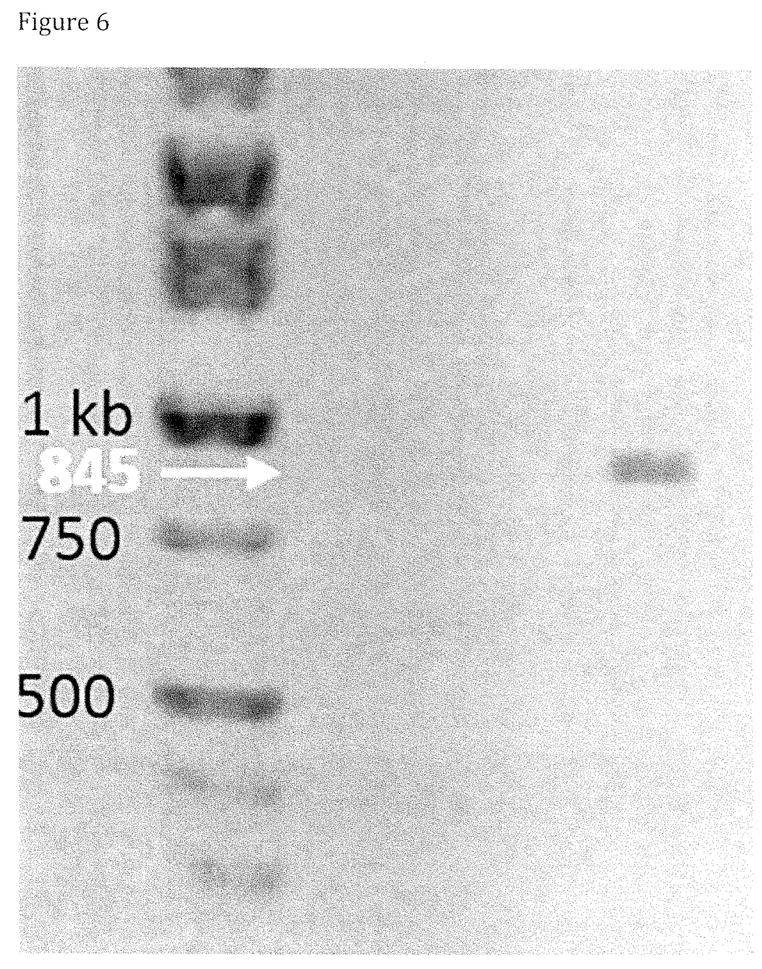
FIG. 6. A gel showing the results when a suspension of *E. coli* in simulated urine with gene for kanamycin resistance is mixed with ammonia, passed through Q-Sepharose, washed, eluted with 1 M NaCl solution, diluted to PCR conditions, and subjected to 20 cycles of PCR. The arrow shows the amplified product, demonstrating that *E. coli* are also disrupted by this universal sample generation process.

To demonstrate that this sample preparation and recovery procedure is truly universal, and includes bacterial cells as well as fungal cells and retrovirus particles, a suspension of *E. coli* carrying the gene for a protein that confers kanamycin resistance in simulated urine was mixed with ammonia, passed through Q-sepharose, washed, eluted with 1 M NaCl solution, diluted to PCR conditions, and subjected to 20 cycles of PCR. The arrow shows the amplified product, demonstrating that *E. coli* are also disrupted by this universal sample generation process. A gel showing the results is presented in FIG. 6.

What is claimed is:

1. A process for extracting from a biological sample, concentrating, and delivering for PCR amplification, nucleic acid molecules from a sample, said process comprising sequentially
   (a) mixing said biological sample with an aqueous ammonia solution having a concentration of 50-250 mM,
   (b) passing the resulting mixture through a solid support to which is immobilized quaternary ammonium moieties,
   (c) washing said support with water,
   (d) washing said support with an aqueous solution of salt,
   (e) collecting a solution containing said nucleic acid molecules, and
   (f) diluting said solution to achieve a salt concentration compatible with a nucleic acid amplification process.

2. The process of claim 1, wherein said solid support is either Q-Sepharose or a strongly basic anion exchange resin.

3. The process of claim 1, wherein said salt is sodium chloride has a concentration of 0.8 to 2.5 M.

4. A process for detecting DNA and/or RNA target molecules from a biological sample in a solution comprising
   (a) mixing said biological sample with aqueous ammonia solution having a concentration of 50-250 mM,
   (b) passing the resulting mixture through a solid support to which is immobilized quaternary ammonium moieties,
   (c) washing said support with water,
   (d) washing said support with an aqueous solution of salt,
   (e) collecting a solution containing said nucleic acid molecules,
   (f) diluting said solution to achieve a salt concentration compatible with a nucleic acid amplification process, and
   (g) amplifying said DNA or RNA target molecules.

5. The process of claim 4, wherein said amplification method is selected from the group consisting of helicase-dependent amplification, recombinase-polymerase amplification, and PCR.

6. The process of claim 5, wherein the primers used in said method contain nucleotide analogs comprising heterocycles independently chosen from the group consisting of 2-aminopurine, 2,6-diaminopurine, 2-thiothymidine, 2-thiouracil, hypoxanthine, $N^4$-ethylcytosine and $N^4$-methylcytosine.

7. The process of claim 5, wherein the primers used in said method contain nucleotide analogs comprising heterocycles independently chosen from the group consisting of 8. The process of claim 5, wherein said amplification is a nested PCR.

9. The process of claim 8, wherein said nested PCR reaction uses external primers that contain nucleotide analogs comprising heterocycles independently chosen from the group consisting of 10. The process of claim 1, wherein said biological sample is blood that is not drawn by an expert professional, urine, feces, vomitus, or sputum.

11. The process of claim 4, wherein said biological sample is blood that is not drawn by an expert professional, urine, feces, vomitus, or sputum.

* * * * *